United States Patent [19]

Toews

[11] Patent Number: Plant 6,229

[45] Date of Patent: Jul. 26, 1988

[54] PEACH TREE, "EARLY MAYCREST"

[76] Inventor: Ronald G. Toews, 17591 E. Huntsman, Reedley, Calif. 93654

[21] Appl. No.: 884,643

[22] Filed: Jul. 11, 1986

[51] Int. Cl.[4] ..... A01H 5/00

[52] U.S. Cl. ..... Plt./43

[58] Field of Search ..... Plt. 43

*Primary Examiner*—James R. Feyrer

*Attorney, Agent, or Firm*—Worrel & Worrel

[57] ABSTRACT

A new and distinct Peach Tree denominated varietally as "Early Maycrest" generally resembling the Maycrest Peach Tree, U.S. Plant Pat. No. 4,064, but bearing a freestone fruit having a yellow flesh and which is mature for harvesting approximately May 12 through May 16, earlier than that of the Maycrest Peach Tree.

1 Drawing Sheet

BACKGROUND OF THE INVENTION

The present invention relates to a new and distinct variety of peach tree, denominated varietally as "Early Maycrest" and which is generally similar in physical characteristics to the "Maycrest" peach tree [U.S. Plant Pat. No. 4,064], of which it is a newly found sport, but from which it is distinguished as to novelty by bearing a more deeply colored fruit having less pubescence than "Maycrest" variety and which ripens for harvesting one week earlier than the Maycrest variety or approximately May 12 through May 16 at Reedley, Calif.

The Maycrest peach tree, [U.S. Plant Pat. No. 4,064], is well known as a vigorous producer of large, firm fleshed and semi-freestone fruit which is ripe for harvesting on approximately May 20 in the San Joaquin Valley of Central California. Furthermore, the fruit of the Maycrest peach tree has long been known for its excellent eating quality and delicious flavor.

It has long been recognized that it would be desirable to have a peach tree that somewhat resembles the Maycrest peach tree but which bears fruit which ripens for harvesting earlier in the season, whereby the commercial demand for large yellow-fleshed peach can be effectively satisfied over a greater period of time.

ORIGIN AND ASEXUAL REPRODUCTION OF THE NEW VARIETY

The new and distinct variety of peach tree hereof was a chance sport which was discovered on the applicant's property located at 17591 East Huntsman, Reedley, Calif., in March of 1982. The sport which was found in a planting of Maycrest peach trees was noted at that time to have desirable characteristics. Bud wood from this sport was thereafter procured by the applicant and thereafter budded into test trees by Douglas Reisner at the Reisner Nursery located at Visalia, Calif. This first asexual propagation resulted in progeny being produced that were found to possess the same distinctive characteristics as the original sport.

SUMMARY OF THE NEW VARIETY

The "Early Maycrest" variety of peach tree is characterized by many of the desirable characteristics of the Maycrest peach tree [U.S. Plant Pat. No. 4,064], but has the important distinction of bearing fruit that is more deeply colored and has less pubescence than the Maycrest variety and which is ripe for harvesting approximately May 12 through May 16, which is earlier than the Maycrest peach tree. The fruit of the subject invention is freestone in nature having a flesh which is lightly yellow colored with no red in the pit cavity at picking time.

BRIEF DESCRIPTION OF THE DRAWING

The accompanying drawing is a color photograph of five mature fruit of the subject variety, one of which has been divided in the suture plane to show the flesh and pit characteristics; together with a twig bearing representative leaves which display the dorsal and ventral coloration thereof.

DETAILED DESCRIPTION

Referring more particularly to the pomological details of this new and distinctive variety of peach tree the following has been observed under the ecological conditions prevailing at the applicant's orchard located at 17591 East Huntsman Avenue, Reedley, Calif. All major color code plate identifications are by reference to the *Dictionary of Color* by Maerz and Paul, Second Edition. However, common color names are also employed occasionally.

TREE

Size: Large.
Figure: Spreading, depending upon pruning practices.
Productivity: Very productive.
Regularity of bearing: Regular.
Trunk:
- *Diameter in relation to length.*—Average.
- *Surface texture.*—Medium.

Branches:
- *Size.*—Medium.
- *Surface texture.*—Average.
- *Color — young growth.*—Pg. 53, Plate 15, J-10.
- *Color — older growth.*—Pg. 55, Plate 16, H-12.
- *Lenticels.*—Numbers — few; Size — small, approximately 2 mm. in diameter.

Leaves:
- *Size.*—Medium.
- *Length.*—Approximately 125 through 135 mm.
- *Width.*—Approximately 30 through 37 mm.
- *Shape.*—Lanceolate with an acuminate apice.
- *Color.*—Dorsal surface — Yew or Brewster Green, Pg. 71, Plate 24, L-1. Ventral surface — Mt. Vernon Green, Pg. 69, Plate 23, L-8.
- *Marginal form.*—Finely serrate.

*Glandular characteristics.*—Numbers — 1 through 3 glands may be found; Position — generally opposite; Form — globose; Color — golden brown.

*Petiole.*—Length — approximately 9 through 11 mm.; thickness — approximately 1.5 through 2 mm.

*Stem glands.*—None evident.

*Stipules.*—Not present.

Flower buds:

*Size.*—Large.

*Shape.*—Obtuse and plump.

*Surface texture.*—Pubescent.

Flowers:

*Date of bloom.*—Full bloom is approximately February 20 in Reedley, Calif.

*Size.*—Large, approximately 45 mm. in diameter.

*Color.*—Dorsal surface — Pg. 25, Plate 1, B-3. Ventral surface — Pg. 25, Plate 1, E-2.

*Pistils.*—Numbers — generally 1.

*Stamens.*—Numbers — approximately 37 through 41.

FRUIT

Maturity:

*Ripe for harvesting.*—May 12 through May 16 in Reedley, Calif.

Size:

*Uniformity.*—Uniform.

*Axial diameter.*—Approximately 69 to 72 mm.

*Diameter transverse in the suture plane.*—Approximately 69 to 72 mm.

*Diameter transverse at right angles to the suture plane.*—Approximately 62 to 64 mm.

Form:

*Uniformity.*—Uniform.

*Symmetry.*—Symmetrical.

*Shape.*—Globose.

*Suture.*—A distinct shallow suture extends from the base to the apex over the entire circumference. The new variety displays a slight depression beyond the pistil point.

*Ventral surface.*—Variable; occasionally slightly rounded, or alternatively somewhat slightly lipped throughout; the sides appear equal.

*Stem cavity.*—Rounded; the stem cavity is elongated in the suture plane and the suture appears on one side of the stem cavity. Depth — approximately 12 mm.; Width — approximately 25 mm.; Length in the suture plane — approximately 32 mm.

*Base.*—Truncate.

*Apex.*—Rounded.

*Pistil point.*—Variable; occasionally apical or sometimes oblique.

*Stem.*—Length — approximately 12 mm.; Width — approximately 3 mm.

*Skin.*—Thickness — medium. Texture — tender. Tendency to crack — slight. Blush — Color — Pg. 33, Plate 5, L-10; ground color — Pg. 41, Plate 9, K-6. Pubescence — scant; short; The pubescence does not round up when rubbed.

Flesh:

*Color.*—Light yellow (Jonquil) Pg. 41, Plate 9, K-5.

*Surface texture of the pit cavity.*—Ridged, yet smooth; no fibers are evident.

*Color of pit well.*—Pg. 45, Plate 11, G-15.

*Amygdalin.*—Scant.

*Juice production.*—Moderate.

*Juice flavor.*—Subacid.

*Aroma.*—Distinct.

*Texture.*—Medium yet meaty.

*Fibers.*—Few.

*Ripening.*—Even.

*Eating quality.*—Good.

Stone:

*Adhesion.*—Full freestone.

*Fibers.*—Length — short.

*Size.*—Generally small; Length — approximately 28 through 31 mm.; Width — approximately 20 mm.; Thickness — approximately 17 through 20 mm.

*Form.*—Generally — oblong; somewhat beaked toward the apex.

*Base.*—Straight.

*Sides.*—Unequal, and somewhat curved on the right side. Irregularly furrowed toward the apex, and pitted toward the base.

*Ridges.*—Rounded.

*Position of grooves.*—The grooves are somewhat shallow, and are located near the apex.

*Color.*—Pg. 43, Plate 10, G-6.

*Tendency to split.*—Slight.

Use: Dessert.

Keeping quality: Good.

Shipping quality: Good.

Resistance to disease: Good.

Although the new variety of peach tree possesses the desirable characteristics noted under the growing conditions prevailing in Reedley, Calif., in the central part of the San Joaquin Valley, at Reedley, it is to be understood that variations of the usual magnitude and characteristics incident to changes in growing conditions, fertilization, pruning and pest control, are to be expected.

Having thus described and illustrated my new variety of Peach Tree, what I claim as new and desire to secure by Plant Letters Patent is:

1. A new and distinct variety of peach tree substantially as illustrated and described which is characterized by bearing a freestone fruit having a yellow flesh and by its general resemblance to the Maycrest Peach Tree, U.S. Plant Pat. No. 4,064, but from which it is distinguished by its bearing fruit which matures for harvesting approximately May 12 through May 16, earlier than that of the Maycrest Peach Tree, and by having a skin color more deeply colored than the Maycrest and having less pubescence than the Maycrest.

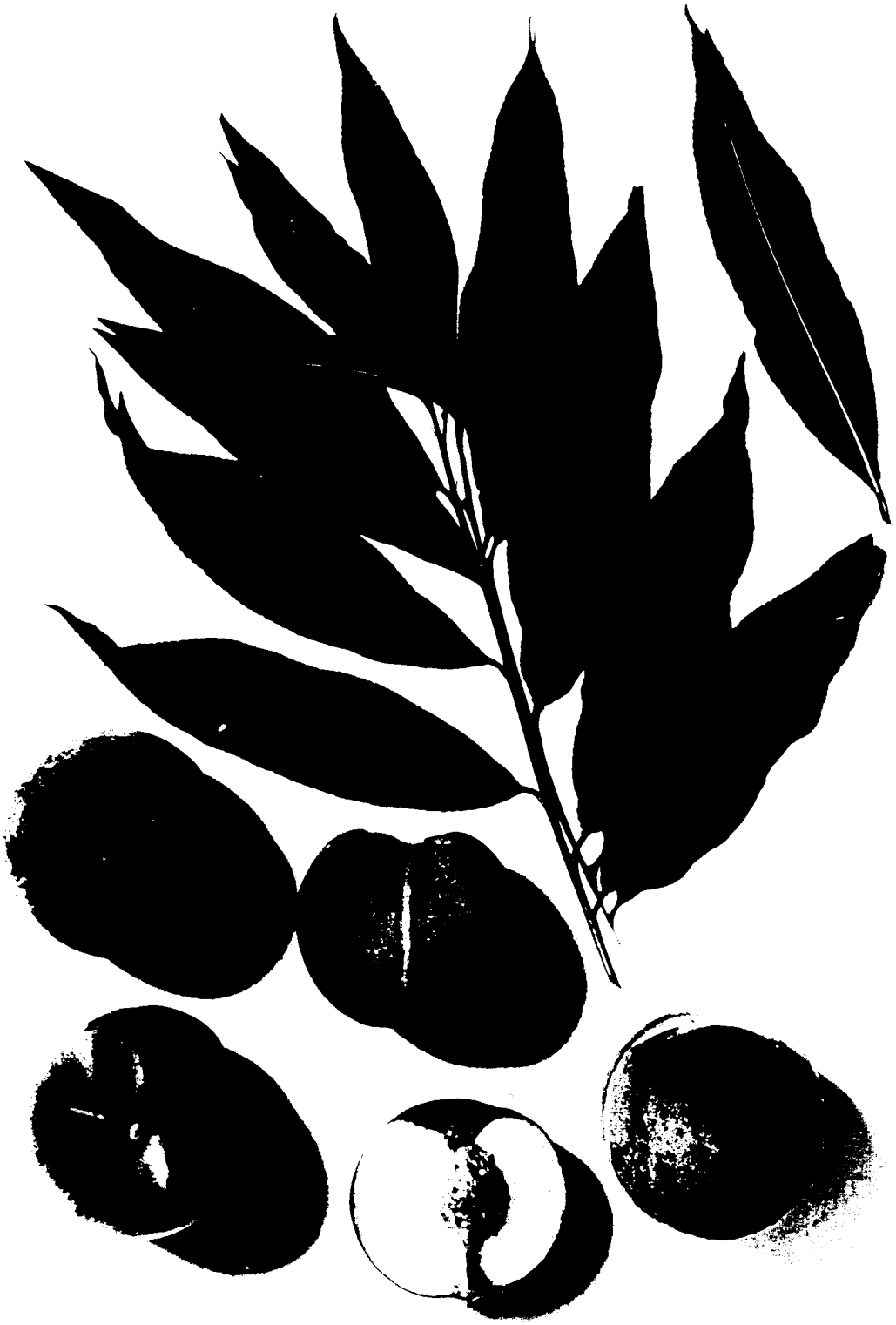

* * * * *